(12) United States Patent
Wong et al.

(10) Patent No.: US 9,814,773 B2
(45) Date of Patent: Nov. 14, 2017

(54) SUSTAINED RELEASE FORMULATIONS FOR DELIVERY OF PROTEINS TO THE EYE AND METHODS OF PREPARING SAME

(75) Inventors: Vernon G. Wong, Menlo Park, CA (US); Louis L. Wood, Potomac, MD (US); Carol Wood, legal representative, Potomac, MD (US); Glenn T. Huang, Fremont, CA (US)

(73) Assignees: Ramscor, Inc., Menlo Park, CA (US); Icon Bioscience, Inc., Sunnyvale, CA (US)

( * ) Notice: Subject to any disclaimer, the term of this patent is extended or adjusted under 35 U.S.C. 154(b) by 170 days.

(21) Appl. No.: 14/124,631

(22) PCT Filed: Jun. 11, 2012

(86) PCT No.: PCT/US2012/041950
§ 371 (c)(1),
(2), (4) Date: Jan. 16, 2014

(87) PCT Pub. No.: WO2013/036309
PCT Pub. Date: Mar. 14, 2013

(65) Prior Publication Data
US 2014/0140992 A1    May 22, 2014

Related U.S. Application Data

(60) Provisional application No. 61/495,672, filed on Jun. 10, 2011.

(51) Int. Cl.
| | | |
|---|---|---|
| *A61K 39/395* | (2006.01) | |
| *A61K 9/00* | (2006.01) | |
| *A61K 47/14* | (2017.01) | |
| *A61K 47/20* | (2006.01) | |
| *A61K 47/34* | (2017.01) | |
| *A61K 38/17* | (2006.01) | |
| *A61K 9/08* | (2006.01) | |

(52) U.S. Cl.
CPC ...... *A61K 39/39541* (2013.01); *A61K 9/0024* (2013.01); *A61K 9/0051* (2013.01); *A61K 9/08* (2013.01); *A61K 38/1709* (2013.01); *A61K 47/14* (2013.01); *A61K 47/20* (2013.01); *A61K 47/34* (2013.01)

(58) Field of Classification Search
None
See application file for complete search history.

(56) References Cited

U.S. PATENT DOCUMENTS

| | | |
|---|---|---|
| 7,550,441 B2 | 6/2009 | Farokhzad et al. |
| 2004/0001889 A1 | 1/2004 | Chen et al. |
| 2008/0038316 A1 | 2/2008 | Wong et al. |

FOREIGN PATENT DOCUMENTS

WO    2008/057867 A2    5/2008

OTHER PUBLICATIONS

Kuno, N. et al., "Recent Advances in Ocular Drug Delivery Systems," Polymers 2011, 3(1):193-221.
Supplementary European Search Report dated Nov. 20, 2014, in related European Application No. 12829655.5, filed on Jun. 11, 2012.
Feczko, T., "Sustained Delivery of Interferons by Micro- and Nanosystems," Recent Patents on Materials Science 2009, vol. 2, pp. 32-42.
Anand, O., Controlled release of insulin and modified insulin from a novel injectable biodegradable gel, published Dec. 2008, pp. 1-119 (online Dissertation), XP-002737685 [retrieved from internet on Jun. 6, 2016] <URL: http://citeseerx.ist.psu.edu/viewdoc/download?doi=10.1.1.692.2608&rep=rep1&type=pdf.

*Primary Examiner* — Yunsoo Kim
(74) *Attorney, Agent, or Firm* — Wiley Rein, LLP (57) ABSTRACT

The present invention provides for injectable pharmaceutical sustained release formulations for delivery of active agents, particularly therapeutic proteins, to the eye. The formulations are biocompatible, biodegradable sustained release formulations comprising low-solubility liquid excipients and relatively small amounts (less than about 10%) of biocompatible, biodegradable polymer such as PLA or PLGA polymers. A unit dose of 5 μL to 100 μL of the formulation provides for sustained release of the agent for at least 14 days.

6 Claims, 7 Drawing Sheets

SUSTAINED RELEASE FORMULATIONS FOR DELIVERY OF PROTEINS TO THE EYE AND METHODS OF PREPARING SAME

RELATED APPLICATION

The present application is a 371 application of International Patent Application No. PCT/US2012/041950, filed Jun. 11, 2012, which claims priority benefit of U.S. Patent Application No. 61/495,672, filed Jun. 10, 2011, and are fully incorporated herein.

FIELD OF THE INVENTION

This invention provides for biocompatible and biodegradable injectable pharmaceutical formulations comprising therapeutic proteins, useful in the treatment of maladies of the eye.

BACKGROUND

Present modes of drug delivery such as topical application, oral delivery, and intramuscular, intravenous and subcutaneous injection may result in high and low blood concentrations and/or shortened half-life in the blood. In some cases, achieving therapeutic efficacy with these standard administrations requires large doses of medications that may result in toxic side effects. The technologies relating to controlled drug release have been attempted in an effort to circumvent some of the pitfalls of conventional therapy. Their aims are to deliver medications on a continuous and sustained manner. Additionally, local control drug release applications are site or organ specific. There remains a need for a more economical, practical, and efficient way of producing and manufacturing drug delivery systems that could be used locally or systemically, in solid, semi-solid, or liquid formulations. In particular, formulations for sustained release in the eye have been developed, yet there is a need for improvement to enhance sustained release of biologics-based medicaments in the eye.

SUMMARY

The present invention provides for liquid sustained release formulations in which the kinetics of active agent release can be controlled using relatively simple formulations comprising at least one non-polymeric liquid excipient (for example, a citrate ester, a benzyl benzoate, or dimethyl sulfone), and a small amount (e.g., less than 10%±1%) of a poly(D,L-lactide) (PLA) or poly(D,L-lactide-co-glycolide) (PLGA) polymer. Additionally, when combined with the non-polymeric excipients of the present invention, PLA and PLGA with or without acid end groups produce different release kinetics. Further, PLGA with different percentages of lactide and glycolide moieties (e.g., lactide:glycolide of 50:50; 65:35; 75:25; or 85:15) yield different sustained release kinetics. Thus, these excipients provide for a variety of formulations from which the release rate of active agent can be sustained for a desired length of time.

Embodiments of the present invention provide for a pharmaceutical formulation for injection into the eye for the sustained release of an active agent comprising: at least one active agent; at least one biodegradable, biocompatible, non-polymeric, liquid excipient selected from the group consisting of benzyl benzoate (BB); esters of benzoic acid with straight, branched, or cyclic chain aliphatic alcohols having one to twenty carbon atoms wherein one of the hydrogen atoms on the aliphatic chain is replaced with a hydroxyl group (e.g., such alcohols as methanol, ethanol, n-propanol, i-propanol, n-butanol, i-butanol, s-butanol, t-butanol, n-pentanol, i-pentanol, neo-pentanol, n-hexanol, cyclohexanol, n-heptanol, n-octonol, n-nonanol, n-decanol, and the like); dimethyl sulfide; dimethyl sulfoxide; dimethyl sulfone; dimethyl sulfozide; mono, di, and tri esters of O-acetylcitric acid or O-propionylcitric acid or O-butyrylcitric acid with $C_1$ to $C_{10}$ straight and branched chain aliphatic alcohols; the mono, di, and tri esters of citric acid with $C_1$ to $C_{10}$ straight and branched chain aliphatic alcohols; triethyl citrate (TEC); triethyl-O-acetyl citrate (TEAC); acetyl triethyl citrate (ATEC); tri-n-butyl citrate; acetyl tri-n-butyl citrate; acetyl tri-n-hexyl citrate; butyryl tri-n-hexyl citrate; or citric acid ethers; d-alpha-tocopherol; d,l-alpha-tocopherol; d-beta-tocopherol; d,l-beta-tocopherol; d-eta-tocopherol; and d,l-eta-tocopherol (including acetate, hemisuccinate, nicotinate, and succinate-PEG ester forms of each of the foregoing); tocopheryl acetate; tocotrienol isomers, tocotrienol esters; and at least one biodegradable, biocompatible poly(D, L-lactide) (PLA) or poly(D,L-lactide-co-glycolide) (PLGA) polymer; wherein the ratio of non-polymeric excipient:polymeric excipient is about 90:10 to about 99:1, inclusive; such that upon initial injection the composition maintains its monolithic integrity in a liquid state; and wherein the composition releases the active agent for a period of at least about 14 days.

The formulations of the present embodiments can be colorless or nearly colorless; can be injectable through a small needle; and can be used in the eye. The formulations of the present embodiments are particularly advantageous for the sustained release of proteins, such as antibodies, in the eye.

In a specific embodiment, the formulation is a unit dosage formulation of about 5 µl to about 100 µl that can injected into the subconjunctiva, periocular space, retrobulbar in the orbit, episclera, intracornea, intrasclera, anterior chamber, anterior segment, posterior chamber, posterior segment, vitreous cavity, subretinal space, suprachorodial segment, or intraretinal area of the eye.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about," which unless otherwise indicated, in relation to percent values, means±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention provides for sustained release formulations in which the kinetics of active agent release can be controlled using relatively simple formulations comprising an excipient (for example, a citrate ester, a benzyl benzoate, dimethyl sulfone), and a small amount (e.g., less than about 10%) of a poly(D,L-lactide) (PLA) or poly(D, L-lactide-co-glycolide) (PLGA) polymer. Additionally, PLA and PLGA with and/or without acid end groups produce different release kinetics. Further, PLGA with different percentages of lactide and glycolide moieties (e.g., lactide:glycolide of 50:50; 65:35; 75:25; or 85:15) yield different sustained release kinetics. Thus, these excipients provide for the design of a variety of formulations from which the release rate of active agent can be sustained for the desired length of time.

The non-polymeric excipients of the present embodiments include benzyl benzoate; esters of benzoic acid with straight, branched, or cyclic chain aliphatic alcohols having one to twenty carbon atoms wherein one of the hydrogen atoms on the aliphatic chain is replaced with a hydroxyl group (e.g., such alcohols as methanol, ethanol, n-propanol, i-propanol, n-butanol, i-butanol, s-butanol, t-butanol, n-pentanol, i-pentanol, neo-pentanol, n-hexanol, cyclohexanol, n-heptanol, n-octonol, n-nonanol, n-decanol, and the like); dimethyl sulfoxide, dimethyl sulfone; dimethyl sulfozide; mono, di, and tri esters of O-acetylcitric acid or O-propionylcitric acid or O-butyrylcitric acid with $C_1$ to $C_{10}$ straight and branched chain aliphatic alcohols; the mono, di, and tri esters of citric acid with $C_1$ to $C_{10}$ straight and branched chain aliphatic alcohols; triethyl citrate; acetyl triethyl citrate; tri-n-butyl citrate; acetyl tri-n-butyl citrate; acetyl tri-n-hexyl citrate; butyryl tri-n-hexyl citrate; and/or citric acid ethers; d-alpha-tocopherol; d,l-alpha-tocopherol; d-beta-tocopherol; d,l-beta-tocopherol; d-eta-tocopherol; and d,l-eta-tocopherol (including acetate, hemisuccinate, nicotinate, and succinate-PEG ester forms of each of the foregoing); tocopheryl acetate; tocotrienol isomers, and their esters. See, e.g., U.S. Pat. No. 7,906,136, No. 7,560,120, and No. 6,960,346; U.S. Patent Pub. 2011/0111006. The non-polymeric excipients of the present embodiments biocompatible in that they are non-toxic and non-irritating, are physically and chemically stable, and do not compromise the stability of a active agent with which they are formulated.

Poly(glycolic acid) (PGA), Poly(lactic acid) (PLA) and their copolymers have been researched for a wide range of applications. These biodegradable aliphatic polyesters have proven biocompatibility and versatile biodegradation properties depending on their molecular weight and chemical compositions: PLA/PGA are biodegradable polyesters that degrade in the body by simple hydrolysis of the ester backbone to non-harmful and non-toxic compounds. The in vivo degradation products are either excreted by the kidneys or eliminated as carbon dioxide and water through well-known biochemical pathways. Typically, active agent has been entrapped in solid poly(D,L-lactide-co-glycolide)-based (PLGA-based) matrices in which release of the agent is achieved by bioerosion of the polymer followed by exposure of previously entrapped agent. See, e.g., U.S. Pat. No. 6,369,116; No. 6,699,493; No. 6,726,918; No. 7,048,946.

Some PLGA-based implants have been made by dissolving polymer in a biocompatible polar aprotic solvent that is miscible to dispersible in body fluid such that, upon administration, the solvent dissipates to produce a solid implant (in situ forming implants). In order for this to occur, the polymer component is present at ≥30 wt. % and the solvent is present at ≤70 wt. %. See U.S. Pat. No. 6,773,714.

In contrast to other polymer-based drug delivery systems, the present embodiments provide for formulations in which the liquid state of the polymer is maintained, and the monolithic integrity of the unit dose is maintained following injection. More specifically, when syringed carefully (e.g., into the eye), the formulations of the present embodiments maintain monolithic integrity in a liquid state, in which the biocompatible, biodegradable excipients are maintained and gradually dissolve over time as the active agent is delivered. The embodiments of the present invention are injectable liquid formulations in which the polymer is present ≤10 wt. % (±1%) of the formulation. For example, the polymer:non-polymer excipient may be prepared in a ratio of polymer excipient:non-polymer excipient(s) that is may be 1:99 to 10:90 (wt. %), inclusive; for example, 5:95 PLGA:TEC (5 wt. % PLGA and 95 wt. % citrate ester). The excipient portion of the formulation can be prepared and then mixed with the active agent. For example, a 5% PLGA in benzyl benzoate (BB) is prepared (e.g., by stirring), and then mixed with immunoglobulin at 2 wt. % (i.e., 2 mg immunoglobulin and 98 mg PLGA:benzyl benzoate).

The formulations of the present invention are injectable through a relatively small gauge syringe needle, for example, a 25, 27, 28, or 30 gauge, or smaller, needle. The unit dose of the formulation for administration in the eye is minute, generally about 5 µL to about 100 µL, inclusive, yet a single unit dose delivers a sustained, therapeutic concentration of active agent for at least 14 days. The formulations of the present invention can be colorless or nearly colorless, which can be advantageous for use in the eye.

The formulations of the present invention are also advantageous for use in the eye because, although liquid, they maintain monolithic integrity when placed in the eye, which is to say they form a contiguous shape and do not disintegrate or disperse into smaller particles or precipitants in the eye. Once administered into the eye, the physician can observe the placement and size of the formulation in the eye, although the subject is not aware of its presence (i.e., the dose of formulation does not obstruct vision). Typically, as long as the formulation is still visible to the physician it is still delivering active agent. This physical characterization is also useful in preparing formulations according to the embodiments herein, because a particular mixture of excipients can readily be prepared and placed in a saline or other fluid environment that mimics conditions in the eye, and observed for maintenance of monolithic integrity.

Regarding polymer excipients that may be used in concert with the non-polymeric excipients of the present embodiments, PLGA is a polymer that, when mixed with particular excipients as described herein, is suitable for sustained release formulations. PLGA can have different amounts of lactide and glycolide moieties (e.g., lactide:glycolide of 50:50; 65:35; 75:25; or 85:15), which affects the sustained release kinetics of the formulation. For example, PLGA 50/50 is a polymer with a 50:50 molar composition of D,L-lactic and glycolic acid in the PLGA chain. See, e.g., U.S. Pat. No. 4,728,721. There are generally three types of PLGA end-groups functions: (i) free carboxylic acid group, (ii) ester terminated group, and (iii) alkyl ester group. Polymers "capped" with ester and alkyl ester groups have different polarity and typically show longer degradation lifetimes than the free carboxylic analogs. Additionally, when used as a solid matrix (e.g., implants or nanoparticles) PLGA polymers having high molecular weight typically release agent more slowly that PLGAs of lower molecular weight. See Gasper et al., 52 J. Control Release 53 (1998).

According to the present embodiments, various PLA, PGA and PLGA polymers can be mixed in liquid excipients as a small percentage (typically about 10% or less) of the volume of the excipient portion of a pharmaceutical formulation, and extend the sustained release profile of agent compared with the release from the liquid excipient alone. Although the use such polymers in solid sustained release formulation has been reported (for example, solid polymer implants, microspheres, or nanospheres), that the addition of a relatively small amount of liquid polymer to a non-polymeric sustained release liquid excipient would modulate the sustained release profile of the non-polymeric excipient is unexpected. Thus, polymer can be used in the formulations of the present invention at about 1%, 2%, 3%, 4%, 5%, 6%, 7%, 8%, 9%, or about 10% (wt/wt), or any fraction thereof, inclusive.

Without being bound by theory, in contrast to current PLGA sustained release compositions and formulations in which active agent is entrapped in the pores of a solid matrix PLGA, in the present embodiments the polymer remains liquid and acts in concert with the liquid, non-polymeric excipient, associating with the liquid excipient and active agent in a loose floating web that disassociates as lactide residues leave the polymer.

The formulations described herein provide for the sustained release of agents such as therapeutic proteins for at least 14 days. This is understood by those of skill in the art to be distinguished from therapeutic effect, which may last for a longer period (or shorter period) than the period over which the therapeutic protein is released from the particular formulation. Release can be sustained for at least 14 days or longer, such as 21 days, 28 days, 35 days, 42 days, 49 days, etc., up to and including 150 days or longer. In this regard, the days or weeks of sustained release can be interpreted and extrapolated from the Figures by one of ordinary skill in the art and are incorporated into the present written description.

The active agents which may be used in the present embodiments include, but are not limited to, anti-glaucoma agents, analgesics, anesthetics, narcotics, angiostatic steroids, anti-inflammatory steroids, angiogenesis inhibitors, nonsteroidal anti-inflammatories, anti-infective agents, anti-fungals, anti-malarials, anti-tuberculosis agents, anti-virals, alpha androgenergic agonists, beta adrenergic blocking agents, carbonic anhydrase inhibitors, mast cell stabilizers, miotics, prostaglandins, antihistamines, antimicrotubule agents, antineoplastic agents, antiapoptotics, aldose reductase inhibitors, antihypertensives, antioxidants, growth hormone antagonists, vitrectomy agents, adenosine receptor antagonists, adenosine delaminate inhibitor, glycosylation antagonists, anti-aging peptides, topoisemerase inhibitors, anti-metabolites, alkylating agents, antiandrigens, anti-oestogens, oncogene activation inhibitors, telomerase inhibitors, antibodies or portions thereof, antisense oligonucleotides, fusion proteins, luteinizing hormone releasing hormones agonists, gonadotropin releasing hormone agonists, tyrosine kinase inhibitors, epidermal growth factor inhibitors, ribonucleotide reductase inhibitors, cytotoxins, IL2 therapeutics, neurotensin antagonists, peripheral sigma ligands, endothelin ETA/receptor antagonists, antihyperglycemics, anti-chromatin modifying enzymes, obesity management agents, anemia therapeutics, emesis therapeutics, neutropaenia therapeutics, tumor-induced hypercalcaemia therapeutics, blood anticoagulants, anti-proliferatives, immunosuppressive agents, tissue repair agents, psychotherapeutic agents, Aptamers (Eyetech), Lucentis (Genentech), RNA inhibitors, insulin, human insulin, GLP-1, and Byetta (exenatide, Amylin).

The formulations of the present invention are particularly advantageous for the sustained release of proteins, in particular, proteinaceous ligands such as antibodies. Antibodies, as used herein means intact immunoglobulin molecules as well as portions, fragments, peptides, analogs or derivatives thereof such as, for example, Fab, Fab', F(ab')$_2$, Fv, CDR regions, paratopes, or any portion or peptide sequence of an antibody that is capable of binding an antigen or epitope, and includes monovalent antibodies, divalent antibodies, polyclonal antibodies, monoclonal antibodies, chimeric antibodies, fully humanized antibodies, recombinant antibodies, and monoclonal antibodies produced by transgenic animals. An antibody is said to be "capable of binding" a molecule if it is capable of specifically reacting with the molecule to thereby bind the molecule to the antibody.

Ocular disorders that may be treated using formulations according to the present embodiments include diabetic retinopathies, proliferative retinopathies, retinal detachment, toxic retinopathies, retinal vascular diseases, retinal degenerations, vascular anomalies, age-related macular degeneration, infectious diseases, inflammatory diseases, ocular ischemia, pregnancy-related disorders, retinal tumors, choroidal tumors, choroidal disorders, vitreous disorders, trauma, cataract complications, dry eye, inflammatory optic neuropathies, and other acquired disorders.

A "disorder" is any condition that would benefit from treatment with, for example, a sustained release agent. This includes chronic and acute disorders or diseases including those pathological conditions which predispose the subject to the disorder in question.

For example, ocular-related disorders in which the vasculature of the eye is damaged or insufficiently regulated. Neovascularization is associated with exudative age-related macular degeneration, diabetic retinopathy, corneal neovascularization, choroidal neovascularization, neovascular glaucoma, cyclitis, Hippel-Lindau Disease, retinopathy of prematurity, pterygium, histoplasmosis, iris neovascularization, macular edema, glaucoma-associated neovascularization, and the like. Disorders associated with both neovascular and atrophic components, such as age-related macular degeneration and diabetic retinopathy, are particularly difficult to treat due to the emergence of a wide variety of complications. Atrophic complications include, for instance, the formation of drusen and basal laminar deposits, irregularity of retinal pigmentation, and accumulation of lipofuscin granules.

The formulations of the present invention can be used for the therapeutic or prophylactic treatment of the eye(s) of a subject. "Therapeutic" refers to the amelioration of the ocular-related disorder, itself, and the protection, in whole or in part, against further ocular-related disease, such as ocular neovascularization or age-related macular degeneration. "Prophylactic" refers to the protection, in whole or in part, against ocular-related disorders, such as ocular neovascularization or age-related macular degeneration. One of ordinary skill in the art will appreciate that any degree of protection from, or amelioration of, an ocular-related disorder is beneficial to a subject. The invention is particularly advantageous in that a therapeutic agent can be directly applied to affected areas of the eye without the harmful side effects of systemic therapies.

Therapeutic proteins that can be formulated according to the present embodiments include cytokines, inhibitors of angiogenesis, neurotrophic agents, steroids, enzymes (e.g., hyaluronidase), and antibodies.

Example inhibitors of angiogenesis include aflibercept (a fusion protein of key binding domains of human VEGFR-1 and -2 combined with a human IgG Fc fragment), pigment epithelium-derived factor (PEDF), anti-VEGF antibody or portion thereof (such as ranibizumab or bevacizumab) angiostatin, vasculostatin, endostatin, platelet factor 4, heparinase, interferons, tissue inhibitor of metalloproteinase 3, and tyrosine kinase inhibitors, and the like. Such factors may prevent the growth of new blood vessels, promote vessel maturation, inhibit permeability of blood vessels, inhibit the migration of endothelial cells, and the like. See, e.g., WO 02/22176.

Another class of therapeutic proteins are neurotrophic factors, which include neuropoietic cytokines, neurotrophins, and the fibroblast growth factors. Ciliary neurotrophic factor (CNTF) is an exemplary of neuropoietic cytokine, that promotes the survival of ciliary ganglionic neurons and supports certain neurons that are NGF-responsive. Neurotrophins include, for example, brain-derived neurotrophic factor and nerve growth factor, perhaps the best characterized neurotrophic factor. Other neurotrophic factors include, for example, transforming growth factors, glial cell-line derived neurotrophic factor, neurotrophin 3, neurotrophin 4/5, and interleukin 1-β. Neuronotrophic factors enhance neuronal survival, and may reverse degradation of neurons. PEDF is an example protein exhibiting anti-angiogenic and neurotrophic activities.

Further regarding antibodies, antibody-based immunosuppressive therapies include anti-IL-2R antibodies (e.g., basiliximab or daclizumab) and anti-CD52 antibodies (e.g., alemtuzumab), abatacept and the affinity-matured belatacept (antibody-based constructs combining the extracellular part of the immunomodulatory CTLA4 receptor with a human IgG Fc region), antithymocyte globulin, muronomab (anti-CD3 antibody), or infliximab (anti-TNF-α). See Thiel et al., 23 Eye 1962 (2009). Additionally, lerdelimumab (anti-TGFb2) human monoclonal antibody has been used in subjects undergoing surgery for glaucoma and cataract.

One of ordinary skill in the art will appreciate that particular therapeutic protein can be modified or truncated (e.g., by recombinant or fragmentation approaches), and retain biological activity. As such, active portions of various proteins (e.g., those portions of anti-angiogenic proteins having biological activity sufficient to inhibit angiogenesis) are also suitable for use in the present formulations.

Cytokines can also be formulated according to the embodiments herein. A "cytokine" refers to any of a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to interleukins IL-1, IL-2, IL-4, IL-5, IL-6, IL-7, IL-10, IL-12, IL-15, IL-18; granulocyte-macrophage colony-stimulating factor (GM-CSF); granulocyte colony-stimulating factor (G-CSF); interferons including interferon-alpha (IFN-α), interferon-beta (IFN-β), and interferon-gamma (IFN-γ); tumor necrosis factor (TNF), transforming growth factor-beta (TGF-β); FLT-3 ligand; and CD40 ligand.

In one embodiment of the present invention, the active agent is a monoclonal antibody. In a specific example formulation, about 2% (wt.) antibody was suspended in a solution of about 5% PLGA (lactide:glycolide 50:50, MW range 7,000-17,000, alkyl ester end group) (Evonik Röhm GmbH, Darmstadt, Germany; Sigma-Aldrich, St. Louis, Mo.), in acetyl triethyl citrate (ATEC). Antibody release from this formulation was sustained for at least 14 days at bioactive and therapeutic levels. In another embodiment, the active agent is a monoclonal antibody suspended in a formulation consisting of about 5% PLGA (lactide:glycolide 65:35, MW range 24,000-38,000, free carboxylic acid end group) in ATEC. Antibody release was sustained at a low level, exhibiting near zero-order kinetics, for at least 14 days, and antibody maintained antigen binding specificity. In yet another embodiment, the active agent is a monoclonal antibody suspended in a formulation consisting of about 6% PLGA (lactide:glycolide 75:25, MW range 4,000-15,000, free carboxylic acid end group) in ATEC. Antibody release was sustained at a low level for at least 14 days, and antibody maintained antigen binding specificity throughout this time period.

In another embodiment, recombinant monoclonal IgG antibody was formulated in 5% PLGA in ATEC or, as control, PBS. Rabbits were administered 50 μL doses containing 1 mg IgG, by bilateral intravitreal injection. Rabbits were humanely euthanized on days 1, 7, 14, and 28 post-administration, and concentrations of test IgG in vitreous humor (pellet and supernatant fractions), retina, choroid, and plasma were compared. Time-points were tested in duplicate or triplicate and averaged. In the plasma, the concentration of IgG from the PBS formulation rose rapidly until it peaked at day 7; whereas the concentration of IgG from the PLGA/ATEC formulation remained lower and leveled off by day 28. In the vitreous, the concentration of IgG from the PBS formulation decreased over time in all tissues; whereas the concentration of IgG from the PLGA/ATEC formulation remained steady in the pellet fraction, and steadily increased in the supernatant fraction; the concentration of IgG from the PLGA/ATEC formulation was higher in both vitreous fractions on day 28 compared with concentration of IgG from the PBS formulation. In the retina and choroid, the concentration of IgG from the PBS formulation spiked initially, then decreased over time. In contrast, the concentration of IgG from the PLGA/ATEC formulation increased steadily over time, and was higher at day 28 in both the retina and choroid compared with the PBS formulation. IgG was delivered to the eye tissues for at least 14 days (i.e., 28 days).

"Treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a disorder of the eye, such as, ocular edema. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

In general, the goal of treatment is reducing the size of a tumor or level of an antigen, or inhibiting the activity of a target, as measured using a suitable in vitro, cellular or in vivo assay. In particular, decreasing the biological activity of a target, antigen or tumor, as measured using a suitable in vitro, cellular or in vivo assay (which will usually depend on the target involved), by at least 5%, 10%, 25%, 50%, 60%, 70%, 80%, or 90%, or 100%, inclusive, as compared with an equivalent untreated control. A decrease refers to a statistically significant decrease. For the avoidance of doubt, a decrease will be at least 5% relative to a reference, such as at least 5%, 10%, 20%, 30%, 40%, 50%, 60%, 70%, 80%, 90%, or more, up to and including 100%, inclusive. Reduce or inhibit can refer to, for example, the symptoms of the disorder being treated, such as the a reduction in ocular pressure or lessening of retinal edema.

An "effective amount" as used herein is any amount that is sufficient either to promote the occurrence of a desired outcome or condition, or to reduce or inhibit the occurrence of an undesired outcome or condition. In some instances a desired outcome or condition is an ideal that represents one end of a spectrum of possible outcomes or conditions. In such instances an effective amount is any amount associated with an outcome or condition that is closer to the desired ideal than would be achieved or observed without the effective amount. Thus, an effective amount promotes the occurrence of a desired outcome or condition, but it need not achieve an ultimate endpoint.

Additional agents and therapies can be combined with the administration of the formulations of the present embodiments. Thus, although the formulations and methods of the invention in certain instances may be useful for replacing existing surgical procedures or drug therapies, the present invention is also useful in improving the efficacy of existing therapies for treating such conditions. Accordingly, combination therapy may be used to treat the subjects that are undergoing or that will undergo a treatment for, inter alia, eye disease or tumor/cancer. For example, the agents of the present invention can be administered in conjunction with anti-microbial agents or anti-proliferative agents. The agents of the invention also can be administered in conjunction with other immunotherapies, such as with antigens, adjuvants, immunomodulators, or passive immune therapy with antibodies. In some embodiments the method according to this aspect of the invention further involves administering to the subject an anti-cancer medicament. The agents of the invention also can be administered in conjunction with nondrug treatments, such as surgery, radiation therapy or chemotherapy. Alternatively, and as indicated by medical condition, the treatment with sustained release therapeutic agents as described herein further involves administering to the subject an antibacterial, antiviral, antimycobial, antifungal, antiparasitic, or other antiinfective medicament. The other therapy may be administered before, concurrent with, or after treatment with the agents of the invention. There may also be a delay of several hours, days and in some instances weeks between the administration of the different treatments, such that the agents of the invention may be administered before or after the other treatment.

As will be understood by those of ordinary skill in the art, the appropriate doses of agents formulated as described herein, with or without additional agents, will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

Pharmaceutical formulations may be conveniently presented in unit dosage form and may be prepared by any of the methods well known in the art of pharmacy. All methods include the step of bringing the active agent, e.g., the therapeutic protein, into association with the excipients of the present invention. In general, the formulations are prepared by uniformly and intimately bringing the agent into association with a liquid excipient containing ≤10% polymer. Formulations for injection may be presented in unit dosage form, e.g., in ampoules or in multi-dose containers The invention is described further in the following non-limiting examples.

EXAMPLES

Example 1. Formulations Comprising Dexamethasone in ATEC with or without PLGA

In general, formulations of dexamethasone in acetyl triethyl citrate (ATEC) were prepared as follows. Poly(D,L-lactide-co-glycolide) (PLGA) or poly(D,L-lactide) (PLA) (Evonik Röhm GmbH, Darmstadt, Germany; Sigma-Aldrich, St. Louis, Mo.) and ATEC were weighed and placed in a 20 mL scintillation vial. The typical lot size was 10 gram total weight, e.g., for a formulation of 5% RG502H (lactide: glycolide 50:50, MW range 7,000-17,000, free carboxylic acid end group) in ATEC: 500 mg of RG502H and 9500 mg of ATEC were weighed, mixed, and stirred in the scintillation vial with a magnetic stir bar. The mixture was stirred at ambient temperature until total dissolution of the polymer. This generally takes several hours to overnight stirring, depending on the polymer used. Once the polymer/ATEC had been mixed to a clear, colorless solution, the desired amount of dexamethasone and the polymer/ATEC solution were weighed, e.g., to make a 6% wt. dexamethasone in 5% RG502H/ATEC, 120 mg of dexamethasone and 1880 mg of 5% RG502H/ATEC were weighed, to make a total of 2 g of the formulation.

For sample preparation, the dexamethasone/polymer/ATEC suspension was vortexed vigorously for 5-10 sec. An aliquot of the formulation mixture was removed with a mechanical pipet and loaded into a BD polypropylene Insulin syringe with a 28 gauge needle (VWR Product #309300). The syringe containing the formulation was weighed (pre-injection weight). A 10 µL aliquot of the formulation was injected into a 20 mL scintillation vial containing 10 mL of 0.9% saline ("release medium"), forming a monolithic shape (e.g., a sphere or "ball") of the formulation at the bottom of the vial. Any excess saline on the syringe was wiped off, and the syringe weighed again (post-injection weight). The actual amount of formulation injected can be calculated by subtracting the post-injection weight from pre-injection weight.

The samples were placed in a 37° C. oven, and at each sampling day, 5 mL of the release-medium was removed for analysis and replaced the with 5 mL of fresh release medium to maintain a 10 mL total volume at all times (maintaining an "infinite sink"). The sampling days were typically day 1, day 3 (or day 4), day 7, day 14, and weekly thereafter until all dexamethasone had been released into the medium from the formulation "ball."

All samples were analyzed by High Performance Liquid Chromatography (HPLC) with the following conditions:
Column: Waters Nova-Pak, C18, 4 um, 150 mm×3.9 mm
Mobile Phase: $H_2O$ ($H_3PO_4$), pH 2.5—acetonitrile, gradient condition from (60:40) to (10:90) in 9 min then returning back to (60:40)
Flow Rate: 0.5 mL/min
Detector: 240 nm
Sample volume: 10 µL
Standard Concentrations: 30 µg/mL, 60 µg/mL, and 120 µg/mL Three formulations were compared, each having 6% dexamethasone in ATEC (6% Dexamethasone/ATEC) either without or with 5% of either RG752H (Poly(D,L-lactide-co-glycolide), lactide:glycolide 75:25, MW range 4,000-15,000, free carboxylic acid end group) (6% Dexamethasone/5% RG752H/ATEC); or PLGA RG502 (Poly(D,L-lactide-co-glycolide), lactide:glycolide 50:50, MW range 7,000-17,000, alkyl ester end group) (6% Dexamethasone/5% RG502/ATEC).

Figure 1:
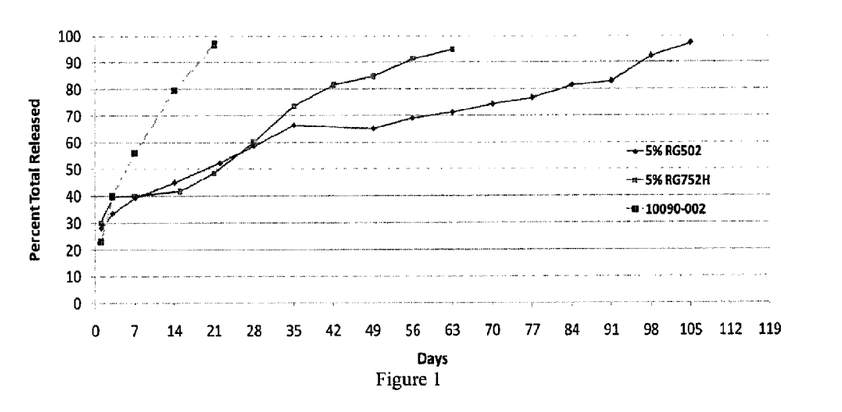
FIG. 1 shows in vitro release profiles of dexamethasone released from three different formulations: 6% Dexamethasone/95% ATEC (■); 6% Dexamethasone/94% (5% RG752H/95% ATEC) (□); 6% Dexamethasone/94% (5% RG502/95% ATEC) (♦).

To analyze in vitro release profiles, an aliquot of 10 µl of each formulation was injected into 10 mL 0.9% saline and incubated at 37° C., then aliquots of 5 mL were exchanged weekly (i.e., infinite sink) and sample was assayed for dexamethasone concentration by standard HPLC method. The resulting sustained release profiles are shown in FIG. 1. As can be seen from the graph in FIG. 1, 10 µl of the formulation of dexamethasone in ATEC sustained the release of dexamethasone for at least 14 days; 10 µl of the formulation of dexamethasone in ATEC/5% RG752 sustained the release of dexamethasone for at least 56 days; and 10 µl of the formulation of dexamethasone in ATEC/5% RG502 sustained the release of dexamethasone for at least 98 days.

Example 2. Formulations Comprising Dexamethasone in ATEC with/without PLA

Four formulations were compared, comprising dexamethasone in ATEC (6% Dexamethasone/ATEC) without or with 5% of either R202H (Poly(D,L-lactide), MW range 10,000-18,000, free carboxylic acid end group) (6% Dexamethasone/5% R202H/ATEC); R203H (Poly(D,L-lactide), MW range 18,000-28,000, free carboxylic acid end group) (6% Dexamethasone/5% R203H/ATEC); or R203S (Poly(D, L-lactide), MW range 18,000-28,000, ester terminated) (6% Dexamethasone/5% R203S/ATEC).

Figure 2:
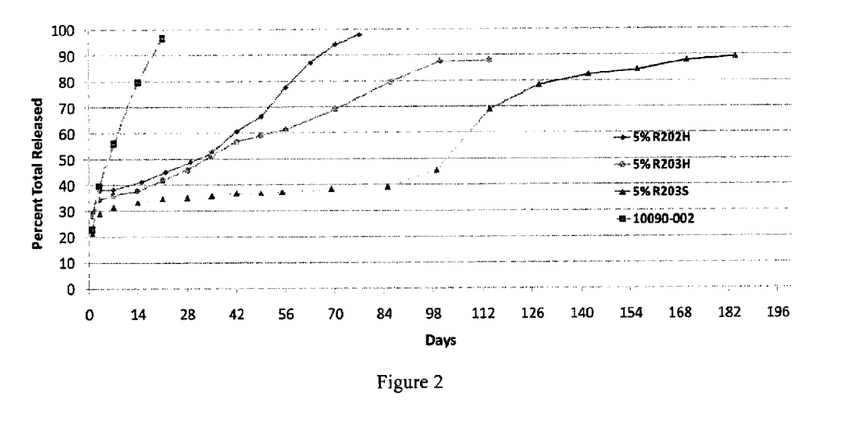
FIG. 2 shows in vitro release profiles of dexamethasone released from four different formulations, each consisting of 6% dexamethasone in the balance of either ATEC (■); 5% R202H/95% ATEC (♦); 5% R203H/95% ATEC (●); or 5% R203S/95% ATEC (▲).

A release profile was generated as in Example 1, and the resulting sustained release profiles are shown in FIG. 2. As can be seen from the graph in FIG. 2, 10 µl of the formulation of dexamethasone in ATEC sustained the release of dexamethasone for at least 14 days; 10 µl of the formulation of dexamethasone in ATEC/5% R202H sustained the release of dexamethasone for at least 70 days; and 10 µl of the formulation of dexamethasone in ATEC/5% R203H sustained the release of dexamethasone for at least 98 days; and 10 µl of the formulation of dexamethasone in ATEC/5% R203S sustained the release of dexamethasone for at least 154 days.

Example 3. Formulations Comprising Dexamethasone in ATEC with/without PLGA

Four formulations were compared, comprising dexamethasone in ATEC (6% Dexamethasone/ATEC) without or with 5% of either PLGA RG502H (6% Dexamethasone/5% RG502H/ATEC); PLGA RG502 (6% Dexamethasone/5% RG502/ATEC); or PLGA RG505 (Poly(D,L-lactide-co-glycolide, D,L-lactide:glycolide 50:50, MW~80,000, alkyl ester end group) (6% Dexamethasone/5% RG505/ATEC). A release profile was generated as in Example 1, and the resulting sustained release profiles are shown in FIG. 3.

Figure 3:
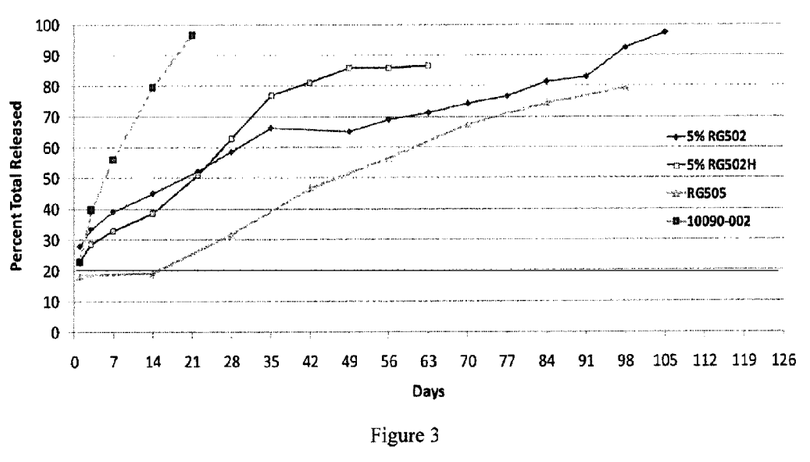
FIG. 3 presents in vitro release profiles of dexamethasone released from four different formulations, each consisting of 6% dexamethasone in the balance of either ATEC (■); 5% RG502H/ATEC (□); 5% RG502/ATEC (♦); or 5% RG505/ATEC (▲).

As can be seen from the graph in FIG. 3, 10 µL of the formulation of dexamethasone in ATEC sustained the release of dexamethasone for at least 14 days; 10 µl of the formulation of dexamethasone in ATEC/5% RG502H sustained the release of dexamethasone for at least 49 days; 10 µl of the formulation of dexamethasone in ATEC/RG502H sustained the release of dexamethasone for at least 98 days; and 10 µl of the formulation of dexamethasone in ATEC/5% RG505 sustained the release of dexamethasone for at least 98 days, with slower release at the outset of the analysis period.

Example 4. Formulations Comprising Dexamethasone, ATEC, and PLGA with Different Lactide:Glycolide Ratios Four formulations were compared, comprising dexamethasone in ATEC (6% Dexamethasone/ATEC) and dexamethasone in ATEC with PLGAs having different percent of lactide and glycolide (i.e., lactide:glycolide ratios of 50:50; 75:25; or 85:15) (6% Dexamethasone/5% RG502H (50:50)/ATEC); RG756S (Poly(D,L-lactide-co-glycolide), 75,25, MW range 76,000-116,000, ester terminated) (6% Dexamethasone/5% RG756S (75:25)/ATEC); PLGA (85:15) Poly (D,L-lactide-co-glycolide), lactide:glycolide (85:15), MW Range 50,000-75,000 (6% Dexamethasone/1.25% PLGA (85:15)/ATEC).

Figure 4:
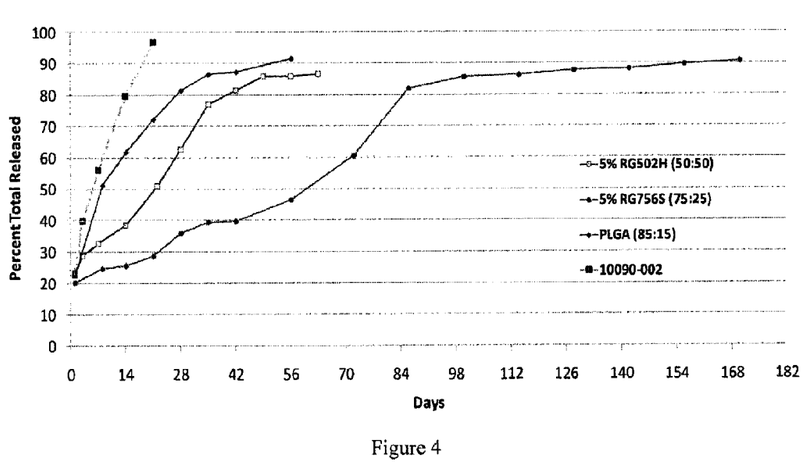
FIG. 4 depicts in vitro release profiles of dexamethasone released from four different formulations, each consisting of 6% dexamethasone in the balance of either ATEC (■); 1.25% PLGA (85:15 lactide:glycolide)/ATEC (♦); 5% RG502H (50:50 lactide:glycolide)/ATEC (□); or 5% RG756S (75:25 lactide:glycolide)/ATEC (●).

A release profile was generated as in Example 1, and the resulting sustained release profiles are shown in FIG. 4. As can be seen in FIG. 4, 10 µl of the formulation of dexamethasone in ATEC sustained the release of dexamethasone for at least 14 days; 10 µl of the formulation of dexamethasone in ATEC/PLGA (85:15) sustained the release of dexamethasone for at least 42 days; 10 µl of the formulation of dexamethasone in ATEC/5% RG502H (50:50) sustained the release of dexamethasone for at least 56 days; and 10 µl of the formulation of dexamethasone in ATEC/5% RG756S (75:25) sustained the release of dexamethasone for at least 84 days.

Example 5. Sustained Release Formulations of Bovine Gamma Globulin (BGG)

A formulation of 1% BGG in 5% PLGA RG502H/ATEC was prepared. Briefly, 1% or 1.5% of fine, powdered γ-globulins from bovine blood (BGG, Cohn fraction II and III, Sigma) were added to a solution of 5% PLGA in ATEC. The resulting suspensions were mixed by vortexing and sonicating until even distribution was observed.

For in vitro sustained release analysis, 10 µL aliquots of the BGG formulation were placed in a matrix of 10 ml 0.9% saline, 1% porcine albumin and 0.05% sodium azide, and incubated at either ambient or 37° C. More specifically, a 20 mL glass release vial was weighed. Then, a 10 µL droplet of the test formulation (suspension) was placed into the glass vial, the total weight of vial and the formulation was measured, and the weight of the added formulation (droplet) calculated. To the vial containing the droplet, 10 mL of release matrix was added. The resulting vial containing the release matrix and the droplet at the bottom of the vial were incubated at wither ambient or 37° C. At each time point, the vial was equilibrated to room temperature, and 5 mL of the matrix solution was carefully withdrawn for BGG determination. Then, 5 mL of the release matrix was added back to the 20 mL glass vial to maintain infinite sink conditions, and the vial returned to incubation at 37° C. Sampling and replacement of matrix were repeated at each time point.

Figure 5:
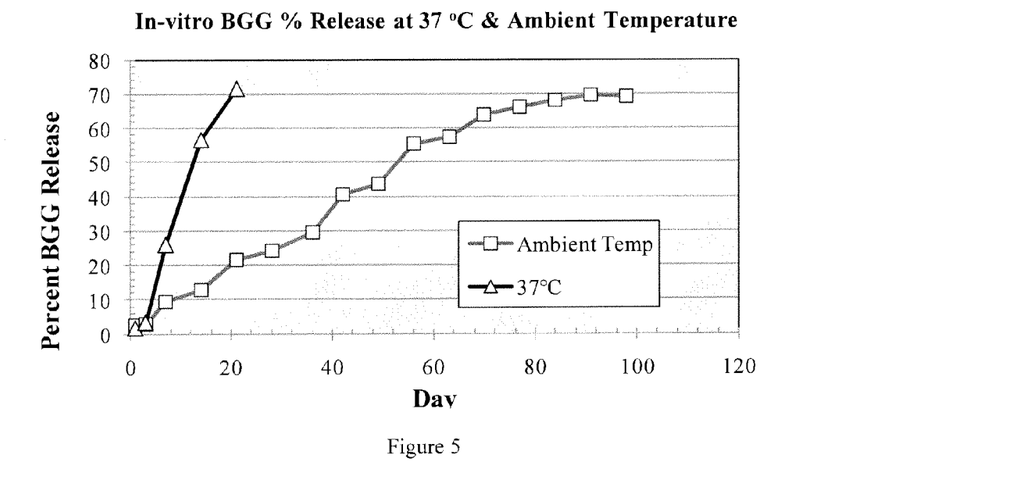
FIG. 5 shows in vitro release profiles of bovine gamma globulin (BGG) released from a formulation of 1% BGG in 5% PLGA RG502H/ATEC at either ambient temperature (□) or 37° C. (Δ). N=10.

BBG determination was performed using Bovine IgG ELISA Quantitation set (Bethyl Laboratories, Inc., Montgomery, Tex.). BGG stock standard (1.00 mg/ml) was prepared in 0.9% saline containing 1% PSA and 0.05% sodium azide and stored at +4° C. for a month. BGG working standards (in the range from 0 ng/mL to 500 ng/mL) were prepared freshly by diluting the stock standard in the assay buffer (also used for sample dilutions). The BGG concentrations were determined against standard calibration curve according to the ELISA Protocol (Bethyl Laboratories, Inc). FIG. 5 was generated. In this formulation, the release of BGG was sustained for at least 16 days at 37° C., and for at least 60 days at ambient temperature.

Example 6. BGG Release Comparing PLGA RGA502H with PLGA RG502

Figure 6:
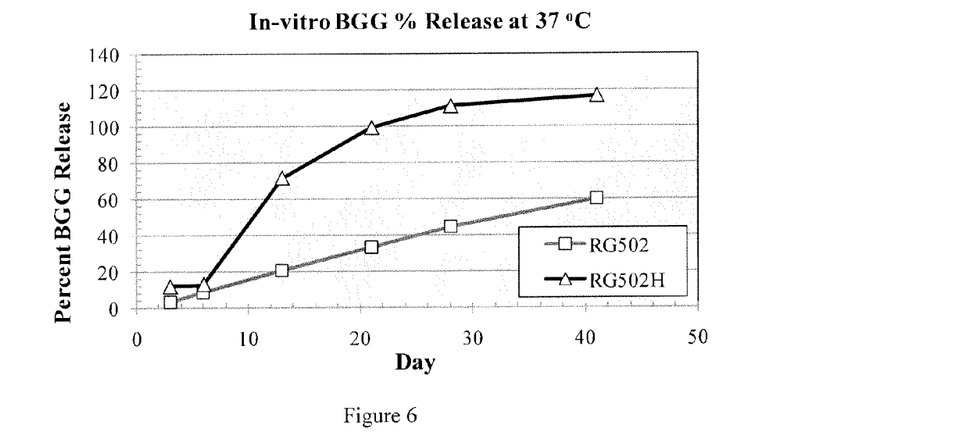
FIG. 6 shows in vitro release profiles of BGG released from formulations of either 1% BGG in 5% PLGA RG502H/ATEC (Δ) or 1% BGG in 5% PLGA RG502/ATEC (□), both formulations maintained at 37° C.

Formulations of 1% BGG in 5% PLGA RG502H/ATEC and 1% BGG in 5% PLGA RG502/ATEC were prepared as in Example 5. FIG. 6 was generated, N=3. The results indicated that BGG was released for at least 14 days from the RG502H/ATEC excipient, and at least 49 days from the RG502/ATEC excipient.

Example 7. Sustained Release of BGG in ATEC/BB/DMSO and 5% PLGA RG502

Figure 7:
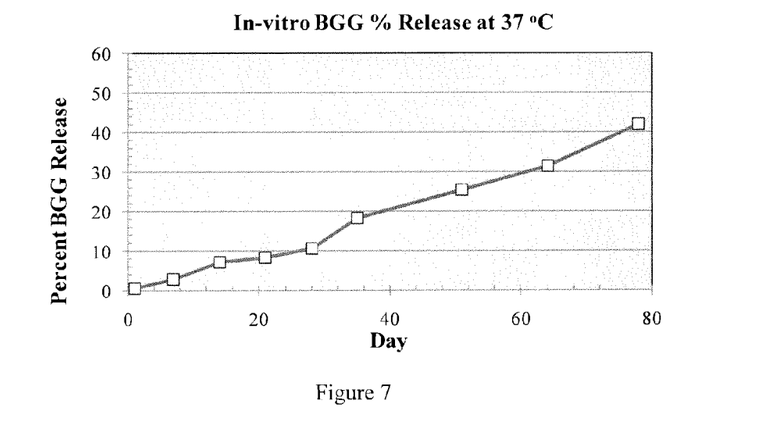
FIG. 7 shows the 37° C. in vitro release profile of BGG released from a formulation of 1% BGG in excipient consisting of 5% PLGA RG502 in ATEC/BB/DMSO (50:38:12).

Formulations of 1% BGG in 5% PLGA RG502 in ATEC/BB/DMSO (50:38:12) were prepared. Data was generated as in Example 5, and graphed and is shown in FIG. 7, N=4. As can be seen from the graph, BGG release was sustained for at least 60 days at 37° C.

Figure 11:
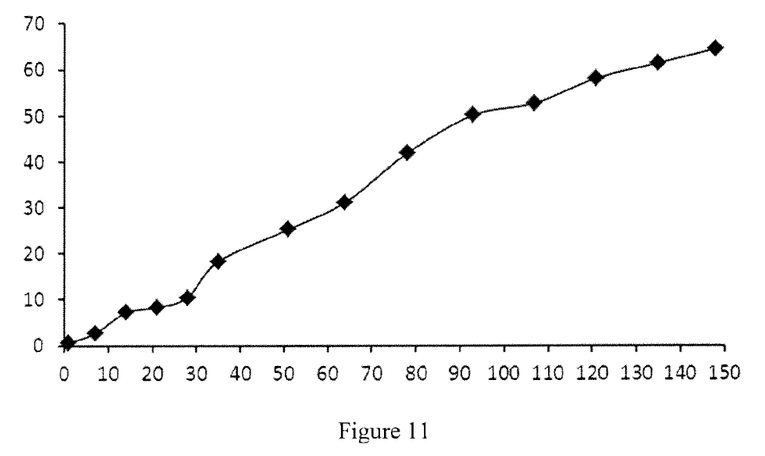
FIG. 11 shows an in vitro release profile of BGG released (ave. %, y-axis) from a formulation of 1.5% BGG in 5% PLGA RG502 in ATEC/BB/DMSO (50:38:12). x-axis, days.

In a similar embodiment, a formulation of 1.5% BGG in 5% PLGA RG502 in ATEC/BB/DMSO (50:38:12) was prepared. When placed in test medium, the formulation formed a monolithic, roughly flat, bolus on the bottom of the vial. An in vitro BGG release profile was generated as shown in FIG. 11. As can be seen from the data, BGG was still being released into the media after 130 days.

Example 8. Comparison of Fresh with Stored Formulation of BGG

Figure 8:
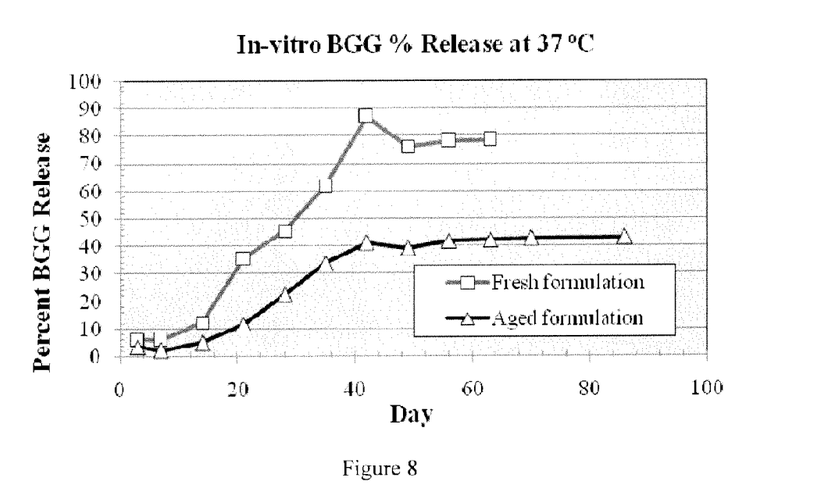
FIG. 8 compares in vitro release profiles of BGG released from a formulation of 1% BGG in 5% PLGA RG502 in ATEC placed in infinite sink conditions either immediately after preparation (□), or after storage for about 24 hours at 4° C. (Δ).

Formulations of 1% BGG in 5% PLGA RG502 in ATEC were prepared and BGG release studied as in Example 5. One formulation was stored for about 24 hr at 4° C. (Aged)

before being subjected to the release study. FIG. 8 was generated, N=3. The formulations that had been stored for about 24 hr at 4° C. (Aged), exhibited slower in vitro release than did freshly (Fresh) made formulations, but in both cases BGG release was sustained for at least 35 days.

Figure 9:
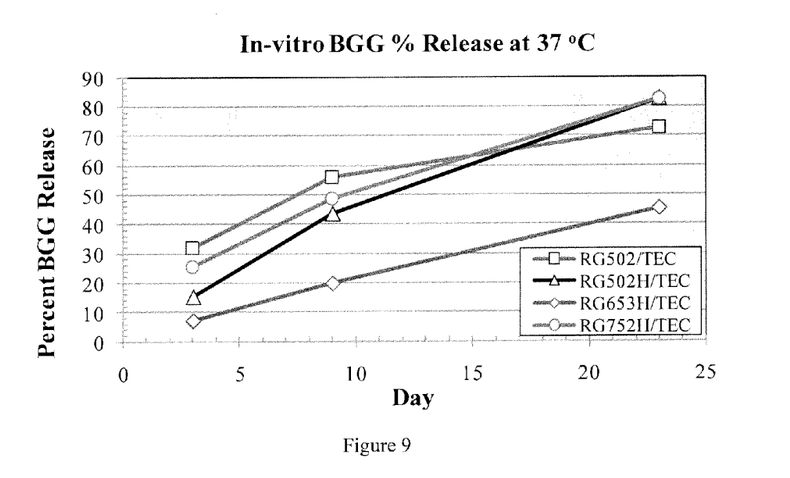
FIG. 9 shows in vitro release profiles of BGG released at 37° C. from formulations of 1% BGG and either 5% RG502/TEC (□); 5% RG502H/TEC (Δ); 5% RG653H/TEC (◇); or 5% RG752H/TEC (○).

Example 9. Sustained Release of BGG from Triethyl Citrate (TEC) and Various PLGAs Formulations of 1% BGG in TEC and 5% PLGA RG502, RG502H, RG653H (Poly(D,L-lactide-co-glycolide), 65:35, MW range 24,000-38,000, free carboxylic acid end group), or RG752H (Poly(D,L-lactide-co-glycolide) 75:25, MW range 24,000-38,000, free carboxylic acid end group) were prepared. FIG. 9 was generated as in Example 5, N=3. In all formulations, BGG release was sustained in vitro for at least 15 days, although the TEC/RG752H formulation can be projected to sustain release for at least 23 days.

Example 10. Sustained Release of BGG from PLGA/ATEC or PLGA/ATEC/DMSO

Figure 12:
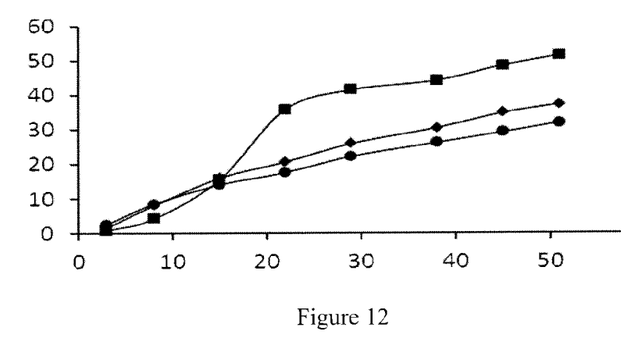
FIG. 12 compares in vitro release profiles of BGG (ave. %, y-axis) released from a 10 μL aliquot of a formulation consisting of 1% BGG in either 7.5% PLGA RG502 in ATEC (◆); 5% PLGA RG502 in ATEC (■); or 7.1% PLGA RG502 in 87.5% ATEC and 4.4% DMSO (●). Formulations had been stored at room temperature for 8 days prior to being placed in infinite sink release conditions. x-axis, days.
Figure 13:
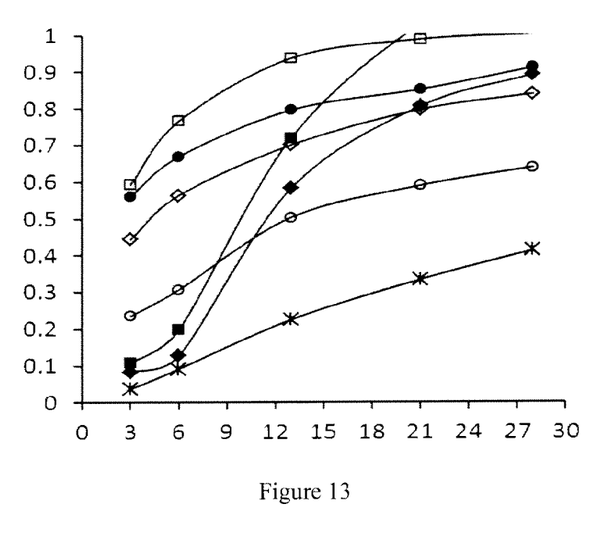
FIG. 13 presents several in vitro release profiles of BGG (ave. %, y-axis) released from a 10 μL aliquot of a formulation consisting of 1% BGG in either 1.25% PLGA (85:15 lactide:glycolide) (balance ATEC in each formulation) (□); 5% PLGA RG653H (●); 5% PLGA RG752H (◇); 5% PLGA RG756S (○); 10% PLGA RG502H (■); 5% PLGA RG502H; or 5% PLGA RG502. x-axis, days.

Three formulations of BGG were prepared by mixing 1% BGG in either 5% PLGA RG502 in ATEC; 7.5% PLGA RG502 in ATEC; or 7.1% PLGA RG502 in 87.5% ATEC and 4.4% DMSO. All formulations were stored at room temperature for 8 days prior to being placed in infinite sink release conditions. When a 10 µL aliquot was placed in infinite sink media, these formulations maintained a rather round monolith on the bottom of the test vial. The results are shown in FIG. 12. BGG was still being released from each formulation at 51 days.

Example 11. Sustained Release of BGG from PLGA/BB/DMSO Formulations

Figure 10:
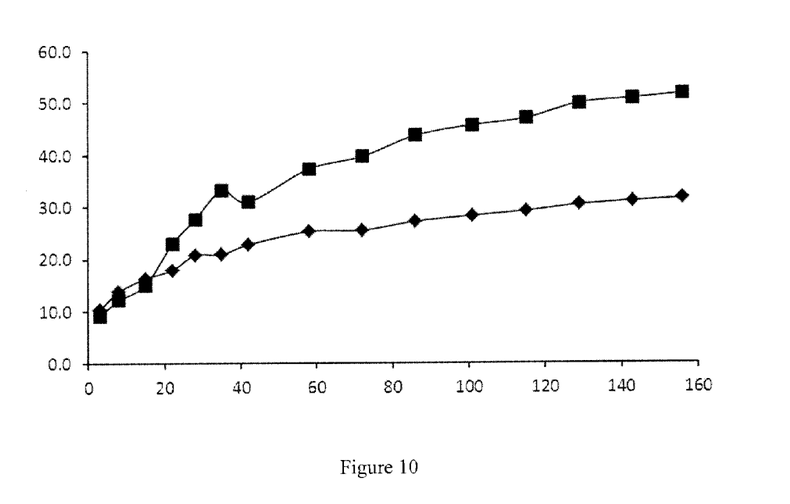
FIG. 10 compares in vitro release profiles of BGG (ave. %, y-axis) released from a formulation of 3% BGG in an excipient consisting of either 1.7% PLGA RG502 in BB:DMSO 75:25 (◆); or 5% PLGA RG502 in BB:DMSO 75:25 (■). x-axis, days; N=4.

Formulations of BGG were prepared by mixing 3% BGG in excipient mixtures consisting of either 1.7% PLGA RG502 in BB:DMSO 75:25; or 5% PLGA RG502 in BB:DMSO 70:25. Results of in vitro release are shown in FIG. 10.

Example 12. Sustained Release of BGG from PLGA/EA/ATEC Formulations

Figure 14:
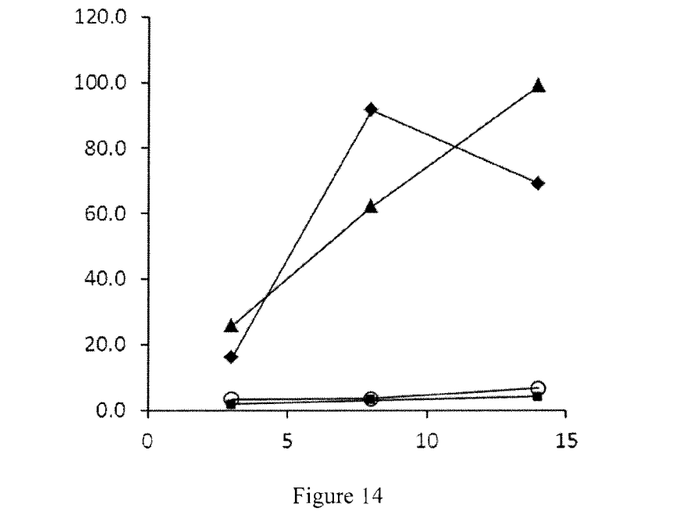
FIG. 14 compares release profiles of BGG (ave. %, y-axis) released from two different size aliquots of formulations consisting of either 1% BGG or 3% BGG in an excipient consisting of 5% PLGA RG502 ATEC:EA 98:2. Aliquots were 10 μL 1% BGG (◆); 50 μL 1% BGG (■); 10 μL 3% BGG (▲); 50 μL 3% BGG (○). N=3; x-axis, days.

Tocopherols provide for another sustained release vehicle with which release rates can be modulated by addition of small amounts of PLGA. Formulations of BGG were prepared by mixing either 1% BGG or 3% BGG in an excipient mixture consisting of 5% PLGA RG502 ATEC:EA 98:2 (i.e. 98% wt ATEC and 2% wt tocopherol acetate). Aliquots of either 10 µL or 50 µL were tested, in triplicate, for in vitro release of BGG, and results are shown in FIG. 14.

Example 13. In Vivo Sustained Release of Antibody in PLGA/ATEC Formulations

Figure 15:
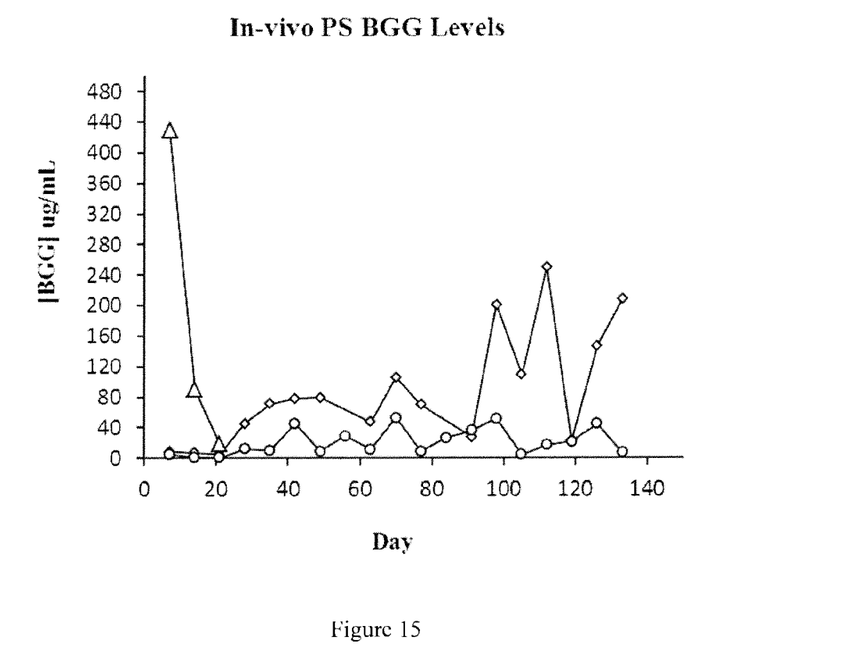
FIG. 15 shows in vivo release of BGG from formulations consisting of either 1% or 3% BGG in an excipient consisting of 5% PLGA R502 in ATEC. A unit dose of 50 μL was injected into the posterior segment of rabbit eyes.

Formulations consisting of either 3% BGG in saline or 1% or 3% BGG in 5% RG502 and ATEC were prepared. A single unit dose of 50 µL was administered to the posterior segment of rabbits, and the release of BGG measured thereafter. As can be seen from FIG. 15, BGG release from 3% BGG in saline was rapid and relatively short-lived in comparison with BGG release from the PLGA/ATEC formulations, which provided for slow release for well over 14 days. Indeed, these data support the conclusion that the present sustained release formulations can release therapeutic doses of therapeutic proteins over long periods of time, and could allow patients to enjoy several weeks or months between injections.

Modifications of the above described modes for carrying out the invention that are obvious to those of ordinary skill in the surgical, pharmaceutical, or related arts are intended to be within the scope of the appended claims.

The invention claimed is:

1. A liquid pharmaceutical formulation for injection into the eye for the sustained release of a therapeutic protein comprising:
   a liquid, biodegradable, biocompatible non-polymeric excipient, wherein said excipient is benzyl benzoate; and
   a biodegradable, biocompatible poly(d,l-lactide-co-glycolide) (PLGA) polymer having a lactide:glycolide ratio of 50:50, MW range 7,000-17,000, and an alkyl ester end group;
   wherein the wt % ratio of non-polymeric excipient:polymer is about 90:10 to 99:1, inclusive;
   wherein upon and following injection of about 5 µL to about 100 µL, inclusive of the formulation, using a 25, 27, 28, 30 gauge, or smaller needle, the formulation maintains its monolithic integrity and liquid state; and
   wherein the formulation releases the therapeutic protein from the liquid formulation for a period of at least about 14 days.

2. The liquid pharmaceutical formulation of claim 1, wherein the formulation is a unit dosage of about 5 µl to about 100 µl that can injected into the subconjunctiva, periocular space, retrobulbar in the orbit, episclera, intracornea, intrasclera, anterior chamber, anterior segment, posterior chamber, posterior segment, vitreous cavity, subretinal space, suprachorodial segment or intraretinal area of the eye.

3. The liquid pharmaceutical formulation of claim 1, wherein the therapeutic protein is an antibody.

4. A method for administering a therapeutic protein to a subject in need thereof comprising administering to the subject's eye an effective amount of the liquid pharmaceutical formulation of claim 1.

5. A syringeable liquid ophthalmic formulation comprising:
   a pharmaceutically active protein in a therapeutically effective amount for a subject in need thereof;
   an amount of benzyl benzoate; and
   a biodegradable, biocompatible poly(d,l-lactide-co-glycolide) (PLGA) polymer having a lactide:glycolide ratio of 50:50, MW range 7,000-17,000, and an alkyl ester end group;
   wherein the wt % ratio of benzyl benzoate:polymer ranges from 90:10 to 99:1, inclusive;
   wherein said pharmaceutically active protein is solubilized or dispersed in said liquid ophthalmic formulation;
   wherein a volume of about 5 µl to about 100 µl inclusive of the liquid ophthalmic formulation is syringeable through a 25, 27, 28, 30 gauge, or smaller, needle; and
   wherein upon injection and thereafter, the liquid ophthalmic formulation maintains a liquid bolus state while the pharmaceutically active protein is released for at least about 14 days.

6. The syringeable liquid ophthalmic formulation of claim 5, wherein the protein is an antibody.

* * * * *